US008906286B2

(12) United States Patent
DeSimone et al.

(10) Patent No.: US 8,906,286 B2
(45) Date of Patent: *Dec. 9, 2014

(54) INTRALUMINAL PROSTHESES HAVING POLYMERIC MATERIAL WITH SELECTIVELY MODIFIED CRYSTALLINITY AND METHODS OF MAKING SAME

(75) Inventors: Joseph M. DeSimone, Chapel Hill, NC (US); Michael S. Williams, Santa Rosa, CA (US)

(73) Assignee: SyneCor, LLC, Durham, NC (US)

(*) Notice: Subject to any disclaimer, the term of this patent is extended or adjusted under 35 U.S.C. 154(b) by 719 days.

This patent is subject to a terminal disclaimer.

(21) Appl. No.: 13/075,483

(22) Filed: Mar. 30, 2011

(65) Prior Publication Data

US 2011/0169198 A1 Jul. 14, 2011

Related U.S. Application Data

(60) Continuation of application No. 11/146,455, filed on Jun. 7, 2005, now Pat. No. 7,919,162, which is a division of application No. 10/701,101, filed on Nov. 4, 2003, now Pat. No. 6,932,930.

(60) Provisional application No. 60/453,317, filed on Mar. 10, 2003.

(51) Int. Cl.
*H05B 6/00* (2006.01)
*A61L 31/14* (2006.01)
*A61L 31/04* (2006.01)

(52) U.S. Cl.
CPC *A61L 31/04* (2013.01); *A61L 31/14* (2013.01)
USPC ....................................................... 264/482

(58) Field of Classification Search
USPC ....................................................... 264/482
See application file for complete search history.

(56) References Cited

U.S. PATENT DOCUMENTS 5,607,467 A 3/1997 Froix
5,618,299 A 4/1997 Khosravi et al.
5,629,077 A 5/1997 Turnlund et al.
(Continued)

FOREIGN PATENT DOCUMENTS

EP 0405284 A2 6/1990
EP 0 895 762 A2 2/1999
(Continued)

OTHER PUBLICATIONS

Cooper, Andrew I., "Polymer Synthesis and Processing Using Supercritical Carbon Dioxide", *Journal of Materials Chemistry* 10, pp. 207-234 (2000).

(Continued)

*Primary Examiner* — Joseph S Del Sole
*Assistant Examiner* — John Robitaille
(74) *Attorney, Agent, or Firm* — Myers Bigel Sibley & Sajovec

(57) ABSTRACT

Methods of manufacturing polymeric intraluminal prostheses include annealing the polymeric material to selectively modify the crystallinity thereof. Annealing may be utilized to selectively modify various properties of the polymeric material of an intraluminal prosthesis, including: selectively increasing the modulus of the polymeric material; selectively increasing the hoop strength of the intraluminal prosthesis; selectively modifying the elution rate (increase or decrease) of a pharmacological agent subsequently disposed on or within the annealed polymeric material; selectively increasing/decreasing stress in the intraluminal prosthesis; and selectively modifying the polymeric material such that it erodes at a different rate.

108 Claims, 3 Drawing Sheets

(56) References Cited

U.S. PATENT DOCUMENTS

| | | |
|---|---|---|
| 5,649,952 A | 7/1997 | Lam |
| 5,670,161 A | 9/1997 | Healy et al. |
| 5,674,192 A | 10/1997 | Sahatian et al. |
| 5,697,967 A | 12/1997 | Dinh et al. |
| 5,723,508 A | 3/1998 | Healy et al. |
| 5,733,327 A | 3/1998 | Igaki et al. |
| 5,733,328 A | 3/1998 | Fordenbacher |
| 5,733,330 A | 3/1998 | Cox |
| 5,741,293 A | 4/1998 | Wijay |
| 5,741,323 A | 4/1998 | Pathak et al. |
| 5,744,958 A | 4/1998 | Werne |
| 5,746,208 A | 5/1998 | Prince |
| 5,749,922 A | 5/1998 | Slepian et al. |
| 5,762,065 A | 6/1998 | Prince |
| 5,762,625 A | 6/1998 | Igaki |
| 5,766,204 A | 6/1998 | Porter |
| 5,766,710 A | 6/1998 | Turnlund et al. |
| 5,769,883 A | 6/1998 | Buscemi et al. |
| 5,770,645 A | 6/1998 | Stamler et al. |
| 5,792,056 A | 8/1998 | Prince |
| 5,799,649 A | 9/1998 | Prince |
| 5,800,507 A | 9/1998 | Schwartz |
| 5,808,060 A | 9/1998 | Hudkins et al. |
| 5,824,049 A | 10/1998 | Ragheb et al. |
| 5,851,217 A | 12/1998 | Wolff et al. |
| 5,860,467 A | 1/1999 | DeSimone et al. |
| 5,868,781 A | 2/1999 | Killion |
| 5,873,904 A | 2/1999 | Ragheb et al. |
| 5,916,585 A | 6/1999 | Cook et al. |
| 5,924,987 A | 7/1999 | Meaney et al. |
| 5,938,653 A | 8/1999 | Pepin |
| 5,938,697 A | 8/1999 | Killion et al. |
| 5,957,971 A | 9/1999 | Schwartz |
| 5,957,975 A | 9/1999 | Lafont et al. |
| RE36,370 E | 11/1999 | Li |
| 5,980,564 A | 11/1999 | Stinson |
| 5,984,957 A | 11/1999 | Laptewicz, Jr. et al. |
| 5,984,963 A | 11/1999 | Ryan et al. |
| 6,004,346 A | 12/1999 | Wolff et al. |
| 6,045,568 A | 4/2000 | Igaki et al. |
| 6,080,177 A | 6/2000 | Igaki et al. |
| 6,080,190 A | 6/2000 | Schwartz |
| 6,096,070 A | 8/2000 | Ragheb et al. |
| 6,113,628 A | 9/2000 | Borghi |
| 6,120,847 A | 9/2000 | Yang et al. |
| 6,139,511 A | 10/2000 | Huter et al. |
| 6,156,062 A | 12/2000 | McGuinness |
| 6,165,196 A | 12/2000 | Stack et al. |
| 6,174,330 B1 | 1/2001 | Stinson |
| 6,176,871 B1 | 1/2001 | Pathak et al. |
| 6,179,867 B1 | 1/2001 | Cox |
| 6,224,626 B1 | 5/2001 | Steinke |
| 6,232,434 B1 | 5/2001 | Stamler et al. |
| 6,240,311 B1 | 5/2001 | Prince |
| 6,240,936 B1 | 6/2001 | DeSimone et al. |
| 6,245,103 B1 | 6/2001 | Stinson |
| 6,251,136 B1 | 6/2001 | Guruwaiya et al. |
| 6,264,671 B1 | 7/2001 | Stack et al. |
| 6,264,683 B1 | 7/2001 | Stack et al. |
| 6,267,769 B1 | 7/2001 | Truwit |
| 6,272,370 B1 | 8/2001 | Gillies et al. |
| 6,298,902 B1 | 10/2001 | DeSimone et al. |
| 6,299,604 B1 | 10/2001 | Ragheb et al. |
| 6,302,907 B1 | 10/2001 | Hijlkema |
| 6,306,422 B1 | 10/2001 | Batich et al. |
| 6,312,457 B1 | 11/2001 | DiMatteo et al. |
| 6,322,490 B1 | 11/2001 | Stack et al. |
| 6,323,256 B1 | 11/2001 | DelMain |
| 6,368,346 B1 | 4/2002 | Jadhav |
| 6,387,124 B1 | 5/2002 | Buscemi et al. |
| 6,413,272 B1 | 7/2002 | Igaki |
| 6,420,397 B1 | 7/2002 | Pan et al. |
| 6,436,132 B1 | 8/2002 | Patel et al. |
| 6,440,405 B1 | 8/2002 | Cooper et al. |
| 6,451,373 B1 | 9/2002 | Hossainy et al. |
| 6,463,317 B1 | 10/2002 | Kucharczyk et al. |
| 6,463,318 B2 | 10/2002 | Prince |
| 6,468,299 B2 | 10/2002 | Stack et al. |
| 6,468,519 B1 | 10/2002 | Uhrich |
| 7,517,919 B2 | 4/2009 | Wang et al. |
| 2001/0020083 A1 | 9/2001 | Stamler et al. |
| 2001/0021871 A1 | 9/2001 | Stinson |
| 2001/0029398 A1 | 10/2001 | Jadhav |
| 2001/0034550 A1 | 10/2001 | Buirge et al. |
| 2001/0037126 A1 | 11/2001 | Stack et al. |
| 2001/0044630 A1 | 11/2001 | Stack et al. |
| 2001/0051822 A1 | 12/2001 | Stack et al. |
| 2002/0013617 A1 | 1/2002 | Matsutani et al. |
| 2002/0042625 A1 | 4/2002 | Stack et al. |
| 2002/0051845 A1 | 5/2002 | Mehta et al. |
| 2002/0077691 A1 | 6/2002 | Nachtigall |
| 2002/0095208 A1 | 7/2002 | Gregorich et al. |
| 2002/0124626 A1 | 9/2002 | Ching et al. |
| 2002/0138133 A1 | 9/2002 | Lenz et al. |
| 2002/0155025 A1 | 10/2002 | Daum |
| 2002/0188342 A1 | 12/2002 | Rykhus et al. |
| 2003/0044514 A1 | 3/2003 | Richard |
| 2003/0105516 A1 | 6/2003 | Austin |

FOREIGN PATENT DOCUMENTS

| | | |
|---|---|---|
| EP | 0693923 B1 | 10/2000 |
| JP | 11137894 A | 5/1999 |
| JP | 2001253962 A | 9/2001 |
| WO | WO 99/59548 | 11/1999 |
| WO | WO 02/098476 A1 | 12/2002 |

OTHER PUBLICATIONS

Engwicht et al., "Characterization of Co-Polymers of Lactic and Glycolic Acid for Supercritical Fluid Processing", *Biomaterials* 21, pp. 1587-1593 (2000).

Herberger et al., "Carbon Dioxide Extraction of Residual Solvents in Poly(lactide-co-glycolide) Microparticles", *Journal of Controlled Release* 90, pp. 181-195 (2003).

Hile et al., "Active Growth Factor Delivery From Poly(D,L-lactide-co-glycolide) Foams Prepared in Supercritical $CO_2$", *Journal of Controlled Release* 66, pp. 177-185 (2000).

Mooney et al., "Novel Approach to Fabricate Porous Sponges of Poly(D,L-lactic-co-glycolic acid) without the use of organic solvents", *Biomaterials*, vol. 17, No. 14, pp. 1417-1422 (1996).

Shakesheff, Kevin "Gently Does It", *Chemistry in Britain*, pp. 30-32 (2003).

Wood et al., "Structural Control in Polymeric Materials Using Supercritical Carbon Dioxide", http://www.liv.ac.uk~aicooper/Bath_2001.pdf.

International Search Report for Int'l Appl'n. No. PCT/US03/33645.

Official Action issued Nov. 13, 2009 by the Japanese Patent Office for corresponding Japanese Patent Application No. 2006-508722.

Official Action issued Jul. 2, 2010 by the Japanese Patent Office for corresponding Japanese Patent Application No. 2006-508722.

Supplemental European Search Report issued Aug. 20, 2010 by the European Patent Office for corresponding European Patent Application No. 04710269.4.

INTRALUMINAL PROSTHESES HAVING POLYMERIC MATERIAL WITH SELECTIVELY MODIFIED CRYSTALLINITY AND METHODS OF MAKING SAME

RELATED APPLICATION

This application is a continuation application of Ser. No. 11/146,455, filed Jun. 7, 2005, now U.S. Pat. No. 7,919,162 which is a divisional application of U.S. patent application Ser. No. 10/701,101 filed Nov. 4, 2003, now issued as U.S. Pat. No. 6,932,930, which claims the benefit of U.S. Provisional Application No. 60/453,317, filed Mar. 10, 2003, the disclosures of which are incorporated herein by reference in their its entireties as if set forth fully herein.

FIELD OF THE INVENTION

The present invention relates generally to medical devices and, more particularly, to intraluminal prostheses.

BACKGROUND OF THE INVENTION

Stents are typically used as adjuncts to percutaneous transluminal balloon angioplasty procedures, in the treatment of occluded or partially occluded arteries and other blood vessels. As an example of a balloon angioplasty procedure, a guiding catheter or sheath is percutaneously introduced-into the cardiovascular system of a patient through a femoral artery and advanced through the vasculature until the distal end of the guiding catheter is positioned at a point proximal to the lesion site. A guidewire and a dilatation catheter having a balloon on the distal end are introduced through the guiding catheter with the guidewire sliding within the dilatation catheter. The guidewire is first advanced out of the guiding catheter into the patient's vasculature and is directed across the vascular lesion. The dilatation catheter is subsequently advanced over the previously advanced guidewire until the dilatation balloon is properly positioned across the vascular lesion. Once in position across the lesion, the expandable balloon is inflated to a predetermined size with a radiopaque liquid at relatively high pressure to radially compress the atherosclerotic plaque of the lesion against the inside of the artery wall and thereby dilate the lumen of the artery. The balloon is then deflated to a small profile so that the dilatation catheter can be withdrawn from the patient's vasculature and blood flow resumed through the dilated artery.

Balloon angioplasty sometimes results in short or long term failure. That is, vessels may abruptly close shortly after the procedure or restenosis may occur gradually over a period of months thereafter. To counter restenosis following angioplasty, implantable intraluminal prostheses, commonly referred to as stents, are used to achieve long term vessel patency. A stent functions as scaffolding to structurally support the vessel wall and thereby maintain luminal patency, and are transported to a lesion site by means of a delivery catheter.

Types of stents may include balloon expandable stents, spring-like, self-expandable stents, and thermally expandable stents. Balloon expandable stents are delivered by a dilitation catheter and are plastically deformed by an expandable member, such as an inflation balloon, from a small initial diameter to a larger expanded diameter. Self-expanding stents are formed as spring elements which are radially compressible about a delivery catheter. A compressed self-expanding stent is typically held in the compressed state by a delivery sheath. Upon delivery to a lesion site, the delivery sheath is retracted allowing the stent to expand. Thermally expandable stents are formed from shape memory alloys which have the ability to expand from a small initial diameter to a second larger diameter upon the application of heat to the alloy.

It may be desirable to provide localized pharmacological treatment of a vessel at the site being supported by a stent. Thus, sometimes it is desirable to utilize a stent both as a support for a lumen wall as well as a delivery vehicle for one or more pharmacological agents. Unfortunately, the bare metallic materials typically employed in conventional stents are not generally capable of carrying and releasing pharmacological agents. Previously devised solutions to this dilemma have been to join drug-carrying polymers to metallic stents. Additionally, methods have been disclosed wherein the metallic structure of a stent has been formed or treated so as to create a porous surface that enhances the ability to retain applied pharmacological agents. However, these methods have generally failed to provide a quick, easy and inexpensive way of loading drugs onto intraluminal prostheses, such as stents. In addition, only small amounts of drugs can be loaded into thin polymeric coatings.

Intraluminal prostheses, such as stents have been developed using various polymeric materials and/or coatings of polymeric materials to overcome the limitations of conventional metallic prostheses. However, it would be desirable to be able to adjust various mechanical properties (e.g., modulus, hoop strength, flexibility, etc.) of polymeric intraluminal prostheses. For example, for intraluminal prostheses used to deliver pharmacological agents, it would be desirable to be able to adjust the elution rate of a pharmacological agent therefrom. As another example, it would be desirable to be able to adjust the degradation rate and/or the nature of degradation of the polymeric material.

SUMMARY OF THE INVENTION

According to embodiments of the present invention, methods of manufacturing polymeric intraluminal prostheses (e.g., formed from polymeric material or having a coating of polymeric material) include annealing the polymeric material to selectively modify the crystallinity or crystalline structure thereof. Annealing may include heating the polymeric material to a temperature between the glass transition temperature and the melting temperature (i.e., $T_g < T_{anneal} < T_m$) of the polymeric material for a period of time sufficient to selectively increase the crystallinity of the polymeric material.

Annealing may include initially heating the polymeric material to a temperature that is higher than the melting temperature (i.e., $T_{anneal} > T_m$) of the polymeric material for a period of time and then quenching the polymeric material to a temperature that is lower than the melting temperature (i.e., $T_{quench} < T_m$) for a period of time sufficient to selectively control or limit the crystallinity of the polymeric material. According to embodiments of the present invention, the quench temperature may be between the glass transition temperature and the melting temperature of the polymeric material (i.e., $T_g < T_{quench} < T_m$). According to embodiments of the present invention, the quench temperature may be lower than the glass transition temperature of the polymeric material (i.e., $T_{quench} < T_g$)

According to embodiments of the present invention, annealing may be utilized to selectively modify various properties of the polymeric material of an intraluminal prosthesis. For example, annealing may include heating the polymeric material to a temperature between the glass transition temperature and the melting temperature (i.e., $T_g < T_{anneal} < T_m$) of the polymeric material for a period of time sufficient to:

selectively increase the modulus of the polymeric material; selectively influence axial flexibility; selectively increase the hoop strength of the intraluminal prosthesis; selectively modify the elution rate (increase or decrease) of a pharmacological agent subsequently disposed on or within the annealed polymeric material; selectively decrease stress in the intraluminal prosthesis during expansion from the contracted configuration; and selectively modify the polymeric material such that it erodes at a different rate (i.e., slower or faster).

Annealing may be performed so as to selectively increase (or vary) crystallinity of one or more isolated portions of the polymeric material of an intraluminal prosthesis. This will allow for customization of intraluminal prostheses and allow for matching to anatomical and physiological environments. For example, crystallinity can be increased in a mid section of an intraluminal prosthesis to enhance mechanical strength and scaffolding capability thereof, while leaving the ends of the device more compliant so as to match the physical compliance of a non-diseased vessel wall.

According to embodiments of the present invention, crystallinity can be increased from about 30% to about 70% or greater in polymeric materials. Crystallinity plays an important role in determining both permeability and biodegradability because of the generally accepted fact that the bulk crystalline phase is inaccessible to water and other permeants. Thus, an increase in crystallinity reduces the permeability by both reducing solubility and increasing the tortuosity of the diffusional pathway.

Increasing crystallinity and orienting (uniaxially or biaxially) crystallites can improve mechanical properties including radial compressive strength and flexibility.

According to embodiments of the present invention, annealing may be performed in the presence of carbon dioxide (i.e., with the intraluminal prosthesis being annealed in contact with a carbon dioxide fluid). According to other embodiments of the present invention, annealing may be preceded by immersing the polymeric material in carbon dioxide.

According to embodiments of the present invention, annealing may be performed in the presence of a nucleating agent disposed on or within the polymeric material. Pharmacological agents disposed on or within the polymeric material may include, but are not limited to, agents selected from the following categories: antineoplastics, antimitotics, antiinflammatories, antiplatelets, anticoagulants, antifibrins, antithrombins, antiproliferatives, antibiotics, antioxidants, immunosuppressives, antiallergic substances, and combinations thereof.

According to other embodiments of the present invention, molecular crosslinking of the polymeric material of an intraluminal prostheses may be modified by subjecting the polymeric material to chemical treatment and/or irradiation. The polymeric material may be subjected to chemical treatment and/or irradiation before, during and/or after annealing. Such treatments may also act as a sterilization step.

According to other embodiments of the present invention, the annealed polymeric material of a prosthesis is impregnated with a predetermined amount of one or more pharmacological agents. According to embodiments of the present invention, a polymeric intraluminal prosthesis is immersed in a mixture of carrier fluid and pharmacological agent(s) such that one or more pharmacological agents are infused within the polymeric material or within a polymeric coating thereof.

DETAILED DESCRIPTION OF THE INVENTION

Figure 1:
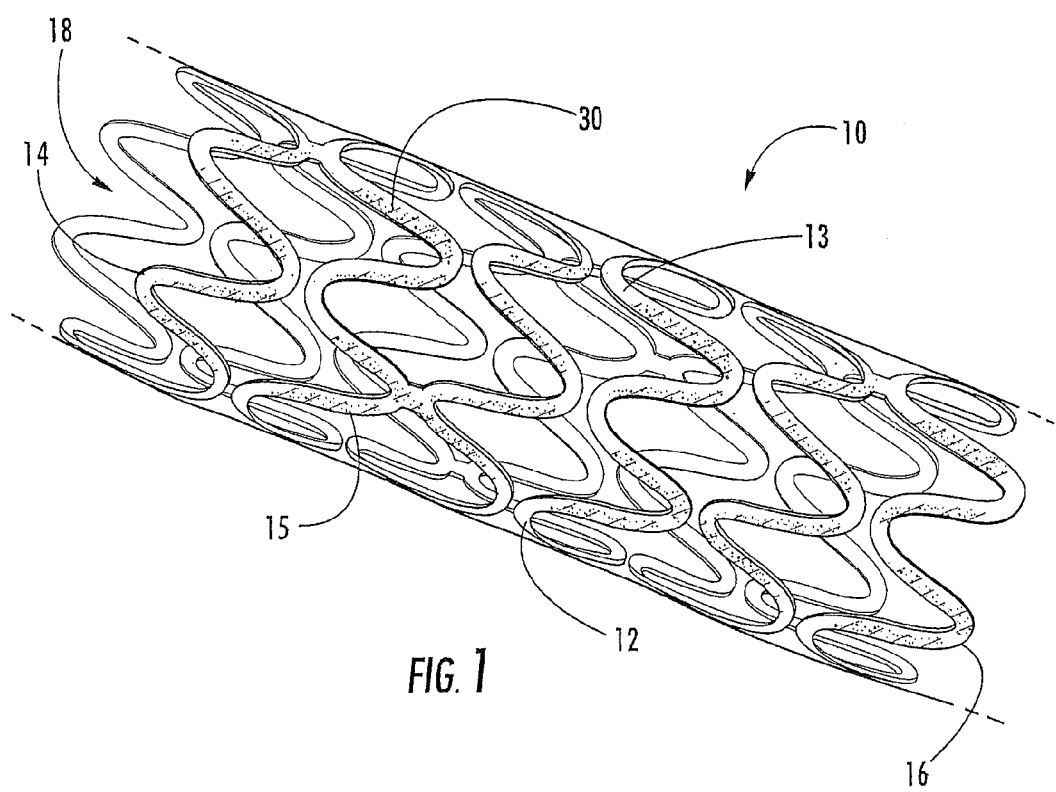
FIG. 1 is a perspective view of an intraluminal prosthesis produced in accordance with embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The term "eluting" is used herein to mean the release of a pharmacological agent from a polymeric material. Eluting may also refer to the release of a material from a substrate via diffusional mechanisms or by release from a polymeric material/substrate as a result of the breakdown or erosion of the material/substrate.

The term "erodible" as used herein refers to the ability of a material to maintain its structural integrity for a desired period of time, and thereafter gradually undergo any of numerous processes whereby the material substantially loses tensile strength and mass. Examples of such processes comprise enzymatic and non-enzymatic hydrolysis, oxidation, enzymatically-assisted oxidation, and others, thus including bioresorption, dissolution, and mechanical degradation upon interaction with a physiological environment into components that the patient's tissue can absorb, metabolize, respire, and/or excrete. The terms "erodible" and "degradable" are intended to be used herein interchangeably.

The term "dosage regimen" is used herein to describe both exogenously administered and internally administered pharmacological agents. A dosage regimen includes both an amount of a pharmacological agent and time(s) that each dose is to be taken. A dosage regimen may also indicate whether a pharmacological agent is to be taken with food or not, and whether other pharmacological agents are to be avoided. A dosage regimen may also indicate the designed rate at which a pharmaceutical agent is released from a substrate.

The term "everolimus" is used herein to mean any member of the macrolide family of pharmacological agents.

The term "hydrophobic" is used herein to mean not soluble in water.

The term "hydrophilic" is used herein to mean soluble in water.

The term "lumen" is used herein to mean any inner open space or cavity of a body passageway.

The terms "polymer" and "polymeric material" are synonymous and are to be broadly construed to include, but not be limited to, homopolymers, copolymers, terpolymers, and the like.

The term "prosthesis" is used herein in a broad sense to denote any type of intraluminal prosthesis, endoprosthesis, or other device which is implanted in the body of a subject for some therapeutic reason or purpose including, but not limited to stents, drug delivery devices, etc.

The term "subject" is used herein to describe both human beings and animals (e.g., mammalian subjects) for medical, veterinary, testing and/or screening purposes.

As used herein, phrases such as "between X and Y" and "between about X and Y" should be interpreted to include X and Y.

As used herein, phrases such as "between about X and Y" mean "between about X and about Y."

As used herein, phrases such as "from about X to Y" mean "from about X to about Y."

Embodiments of the present invention can be employed in conjunction with a number of manufacturing processes associated with producing intraluminal prostheses including, but not limited to, extrusion, pultrusion, injection molding, compression molding, etc. Moreover, embodiments of the present invention may be utilized in batch, semicontinuous, and/or continuous manufacturing processes.

Referring now to FIG. 1, an intraluminal prosthesis 10, that may be produced according to embodiments of the present invention, is illustrated. The illustrated prosthesis 10 is a stent and includes a tubular body portion 12 having a first end 14, a second end 16, and a flow passage 18 defined therethrough from the first end 14 to the second end 16. The body portion 12 is sized for intraluminal placement within the vasculature of a subject and is expandable from a first, reduced cross-sectional dimension (i.e., contracted configuration) to a second enlarged cross-sectional dimension (i.e., expanded configuration) so that the body portion 12 can be transported intraluminally to a treatment site and then expanded to the second enlarged cross-sectional dimension so as to engage and support the vascular wall at the treatment site.

The body portion 12 is formed at least in part from an erodible, polymeric material and/or a coating of erodible, polymeric material. One or more portions of the body portion 12 may be formed from non-erodible material and/or a coating of non-erodible material. The polymeric material may comprise polymers oriented uniaxially and/or biaxially. Exemplary erodible materials that may be utilized in accordance with embodiments of the present invention include, but are not limited to, surgical gut, silk, cotton, poly(hydroxybutyrate), polycarbonates, polyacrylates, polyanhydrides, poly(ortho esters), poly(phosphoesters), polyesters, polyamides (such as polyamides derived from D-glucose), polyphosphazenes, poly(p-dioxane), poly(amino acid), polyglactin, and copolymers thereof, erodable hydrogels, natural polymers such as collagen and chitosan, etc. See, e.g., U.S. Pat. No. 5,723,508 to Healy et al. Particular examples of suitable erodible polymers include, but are not limited to, aliphatic polyester polymers such as poly(lactic acid), poly(L-lactic acid), poly(D,L-lactic acid), poly(glycolic acid), poly(D-lactic-co-glycolic acid), poly(L-lactic-co-glycolic acid), poly(D,L-lactic-co-glycolic acid), poly($\epsilon$-caprolactone), poly(valerolactone), poly(hydroxy butyrate) (including poly (hydroxy butyrate valerate)), poly(hydrovalerate), polydioxanone, poly(propylene fumarate), etc., including copolymers thereof such as polylactic acid-polyethylene glycol block copolymer, and poly(ethyleneoxide)-poly(butylenetetraphthalate), poly(lactic acid-co-trimethylene carbonate), poly(lactic acid-co-lysine), poly($\epsilon$-caprolactone copolymers), poly(L-lactic acid copolymers), etc. See, e.g., J. Oh et al., PCT Application WO 99/59548 at page 2. Additional examples of erodible polymers are set forth in U.S. Pat. No. 5,916,585 to Cook et al., which is incorporated herein by reference in its entirety. The molecular weight (that is, average molecular weight) of the polymer may be from 1,000, 10,000, 100,000 or 500,000 to 2,000,000 or 4,000,000 Daltons, or more.

According to embodiments of the present invention, one or more pharmacological agents (represented by stippling 15) may be infused within the erodible, polymeric material 13 of the body portion 12, or within an erodible coating surrounding the body portion 12, or portions thereof. The body portion material 13 and/or coating is configured to allow the one or more pharmacological agents 15 infused therein to elute, preferably at a predetermined, controlled rate.

Pharmacological agents suitable for inclusion in prosthesis materials and/or coatings, according to embodiments of the present invention include, but are not limited to, drugs and other biologically active materials, and may be intended to perform a variety of functions, including, but not limited to: anti-cancer treatment (e.g., Resan), anti-clotting or anti-platelet formation, the prevention of smooth muscle cell growth and migration on a vessel wall, and cell cycle inhibitors. Pharmacological agents may include antineoplastics, antimitotics, antiinflammatories, antiplatelets, anticoagulants, antifibrins, antithrombins, antiproliferatives, antibiotics, antioxidants, immunosuppressives, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., TAXOTERE® from Aventis S. A., Frankfurt, Germany) methotrexate, azathioprine, vincristine, vinblastine, fluorouracil, doxorubicin hydrochloride (e.g., ADRIAMYCIN® from Pharmacia & Upjohn, Peapack N.J.), and mitomycin (e.g., MUTAMYCIN® from Bristol-Myers Squibb Co., Stamford, Conn.). Examples of such suitable antiinflammatories include glucocorticoids such as dexamethasone, methylprednisolone, hydrocortisone and betamethasone and non-steroidal antiinflammatories such as aspirin, indomethacin and ibuprofen. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX™ (Biogen, Inc., Cambridge, Mass.) Examples of such cytostatic or antiproliferative agents include actinomycin D as well as derivatives and analogs thereof (manufactured by Sigma-Aldrich, Milwaukee, Wis.; or COSMEGEN® available from Merck & Co., Inc., Whitehouse Station, N.J.), angiopeptin, angiotensin converting enzyme inhibitors such as captopril (e.g., CAPOTEN® and CAPOZIDE® from Bristol-Myers Squibb Co., Stamford, Conn.), cilazapril or lisinopril (e.g., Prinivilo and PRINZIDE® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include alphainterferon, genetically engineered epithelial cells, and dexamethasone.

According to embodiments of the present invention, other agents, such as heat sensitive biologics (e.g., transfection vectors, genetic material, tissue material, etc.) may be infused within the erodible polymeric material 13 of the body portion 12, or within an erodible coating surrounding the body portion 12, or portions thereof.

U.S. Pat. No. 4,994,033 to Shockey et al.; U.S. Pat. No. 5,674,192 to Sahatian et al. and U.S. Pat. No. 5,545,208 to Wolff et al. disclose catheters comprising, absorbable/biodegradable polymers or hydrogels containing the desired dosage of a drug. Stents incorporating drug delivery may be found, for, example, in U.S. Pat. No. 5,766,710 to Turnlund et al.; U.S. Pat. No. 5,769,883 to Buscemi et al.; U.S. Pat. No. 5,605,696 to Eury et al.; U.S. Pat. No. 5,500,013 to Buscemi et al.; U.S. Pat. No. 5,551,954 to Buscemi et al. and U.S. Pat. No. 5,443,458 to Eury, each of which is incorporated herein by reference in its entirety.

If a plurality of pharmacological agents are utilized, the plurality of pharmacological agents may be homogeneously distributed on the body portion 12, or heterogeneously distributed on the body portion 12.

According to embodiments of the present invention, a release agent (represented by cross-hatching 30) may be coated on the body portion 12 or incorporated within the body portion 12. The release agent 30 is configured to release a pharmacological agent 15 in a predetermined manner. Multiple release agents may be utilized. For example, if multiple pharmacological agents are utilized, multiple release agents may be utilized.

Figures 2, 3:
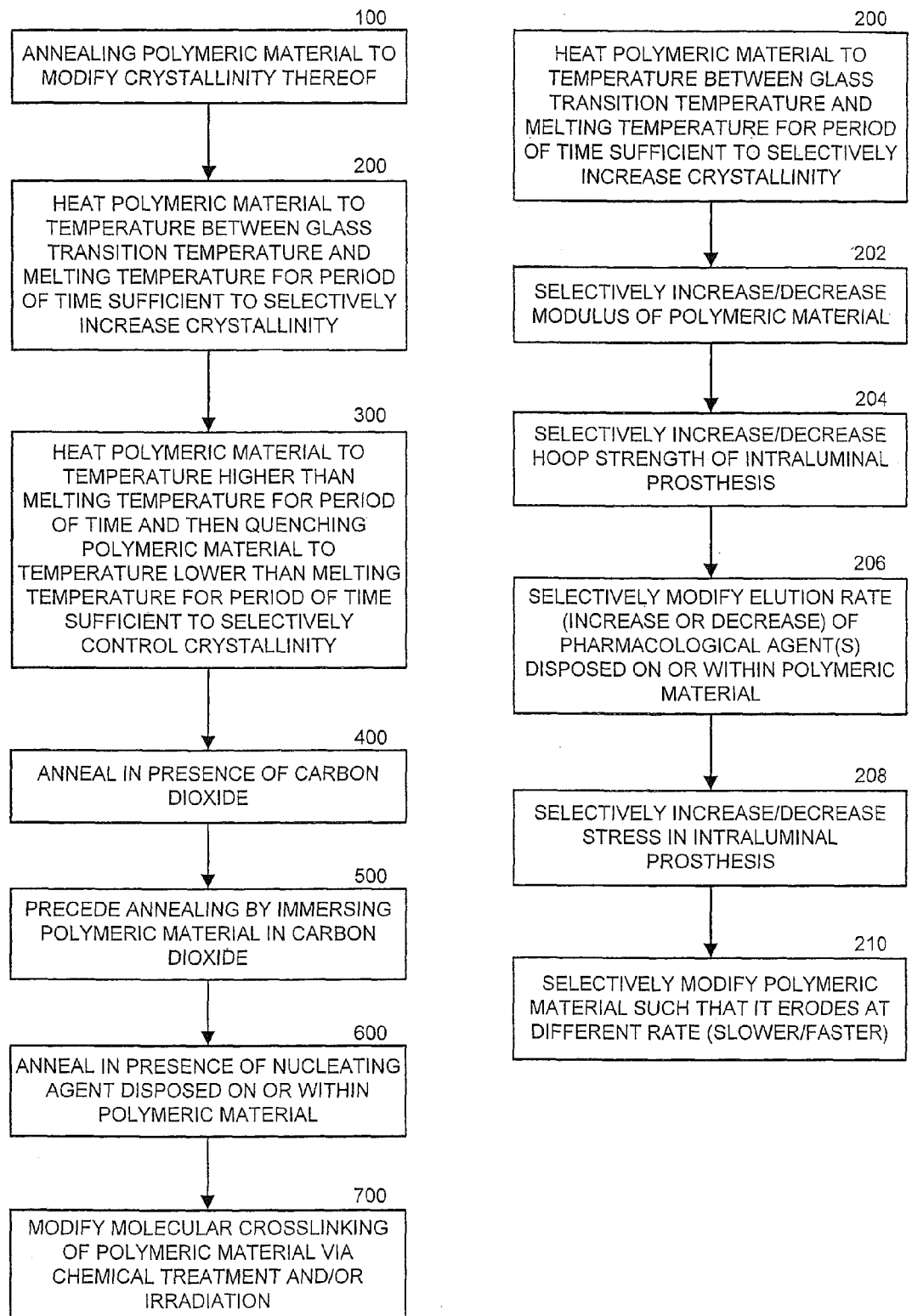
FIGS. 2-4 are flowcharts of operations for manufacturing polymeric intraluminal prostheses, according to embodiments of the present invention.

Referring now to FIG. 2, methods of manufacturing polymeric intraluminal prostheses (e.g., stents, drug delivery devices, etc.) include annealing the polymeric material to selectively modify the crystallinity thereof (Block 100). The term "selectively" is used herein to indicate that a physical property of the polymeric material of an intraluminal prosthesis can be accurately controlled and modified to specific parameters via annealing. Annealing may include heating the polymeric material to a temperature between the glass transition temperature and the melting temperature (i.e., $T_g<T_{anneal}<T_m$) of the polymeric material for a period of time sufficient to selectively increase the crystallinity of the polymeric material (Block 200).

An exemplary polymeric material for intraluminal prostheses according to embodiments of the present invention may have a melting temperature between about 173° C.-178° C. and a glass transition temperature of between about 60° C.-65° C. However, embodiments of the present invention are not limited to polymeric materials with melting temperatures and glass transition temperatures in these ranges. Polymeric materials having various other melting temperatures and glass transition temperatures can be used, without limitation.

Annealing may include initially heating the polymeric material to a temperature that is higher than the melting temperature (i.e., $T_{anneal}>T_m$) of the polymeric material for a period of time and then quenching the polymeric material to a temperature that is lower than the melting temperature (i.e., $T_{quench}<T_m$) for a period of time sufficient to selectively control (i.e., limit the extent of or control the quality or nature of) the crystallinity of the polymeric material (Block 300). According to embodiments of the present invention, the quench temperature may be between the glass transition temperature and the melting temperature of the polymeric material (i.e., $T_g<T_{quench}<T_m$). According to embodiments of the present invention, the quench temperature may be lower than the glass transition temperature of the polymeric material (i.e., $T_{quench}<T_g$).

Referring to FIG. 3, annealing to modify crystallinity may be utilized to selectively modify various properties of the polymeric material of an intraluminal prosthesis. For example, annealing may include heating the polymeric material to a temperature between the glass transition temperature and the melting temperature (i.e., $T_g<T_{anneal}<T_m$) of the polymeric material for a period of time sufficient to: selectively increase or decrease the modulus of the polymeric material (Block 202); selectively increase or decrease the hoop strength of the intraluminal prosthesis (Block 204); selectively modify the elution rate (increase or decrease) of a pharmacological agent subsequently disposed on or within the annealed polymeric material (Block 206); selectively increase or decrease stress in the intraluminal prosthesis (Block 208); and selectively modify the polymeric material such that it erodes at a different rate (i.e., slower or faster) (Block 210).

As is known to those skilled in the art, a change in polymer crystallization is an important way to modify physical properties of polymer materials. The degree and nature of crystallization can have noticeable effects on the physical properties of polymer materials. As used herein, "degree of crystallization" refers to the total amount of crystallinity of a polymer (e.g., as determined by wide angle x-ray scattering (WAXS) or by differential scanning calorimetry (DSC)). As used herein, "nature of crystallization" refers to the exact morphology of crystallites, whether they are large crystallites or small crystallites, or some specific morphology such as spherulitic, elongated, deformed, line nucleated, or a "shish-ka-bob" type structure or some other morphology, at the same overall degree of crystallinity.

The state of order of polymers can extend from the completely random (amorphous) to the completely ordered (perfect crystal). The physical structures that are found depend not only on the configuration and conformation of the molecules, but also by the experimental conditions with which the polymers that make up the intraluminal device or the coating on the intraluminal device were exposed to. Crystallinity is strongly influenced by the crystallization conditions and it includes frozen-in, non-equilibrium states. The crystallization conditions, however, will not only influence the overall amount of crystallinity, but it will also influence the detailed morphology of the sample.

Essentially all polymers exhibit a necking effect on stretching within a specific temperature region. The effect can be recognized by the formation of a neck during elongation due to the occurrence of a constriction after the upper flow limit is reached. The cross section of this constriction continues to decrease up to the lower flow limit. With continued elongation, the cross section of this constriction remains practically constant, but the length of the constricted portion continues to increase at the expense of the rest of the sample. It is sometimes desirable to manufacture intraluminal devices, such as stents, out of precursor stock material that is unoriented. It is sometimes desirable to manufacture intraluminal devices, such as stents, out of precursor stock material that is uniaxially oriented. It is sometime desirable to manufacture intraluminal devices, such as stents, out of precursor stock material that is biaxially oriented. Stents can be oriented or stretched upon deployment using balloon techniques. The degree and nature of the orientation can affect: the mechanical properties of the intraluminal device or the coating on the intraluminal device; the elution profile of the drug or drugs infused within it or coated onto it; and the biodegradation or bioabsorption of the intraluminal device or the coating on the intraluminal device.

Examples of uniaxial orientation include, but are not limited to, 1x-4x, where "x" equals the axial dimension of the original specimen. Examples of biaxial orientation include, but are not limited to, 4x:1x, 3x:2x; where "x" equals the pre-oriented dimension of the specimen, and where "#x" equals the end dimension of the specimen post-orientation. Biaxial implies application of a deforming load in two dimensions, each perpendicular to the other.

The crystallinity of partially crystalline polymers during elongation can increase, decrease, or remain constant. Chain orientation, on the other hand, increases continuously during elongation. With thermally quenched samples having a low degree of crystallinity, the available crystallites are first oriented in the stress direction. The amorphous regions can then crystallize. Annealed polymers, however, can be more highly crystalline. The stress-strain diagrams of stretched polymers differ significantly from those of unstretched polymers. The absence of an upper flow limit, that is the absence of cold flow, is common.

Polymeric materials that have higher degrees of crystallinity and chain orientation can have a higher modulus, which may be useful to increase the hoop strength of polymeric intraluminal devices, such as stents. As is known to those skilled in the art, modulus is a measure of how well a material resists deformation, and is measured by calculating stress and dividing by elongation. Upon deployment using angioplasty balloons, polymeric stents can be stretched, the degree of stress that builds up upon stretching will be influenced by the degree of crystallinity and the orientation of the polymeric chains relative to the orientation of the stretching during deployment.

In addition to affecting the mechanical properties, the degree and nature of the crystallinity in a sample can play a significant role in modifying the elution profile of a drug infused within the sample as well as influence the rate of absorption or degradation of the polymeric stent or the polymeric coating on a stent.

According to embodiments of the present invention, crystallinity of polymeric intraluminal prostheses can be increased from about 30% to about 70% or greater. This increase in crystallinity reduces permeability by both reducing solubility and increasing the tortuosity of the diffusional pathway. Increasing crystallinity and orienting (uniaxially or biaxially) crystallites also improves mechanical properties including radial compressive strength and flexibility.

Referring back to FIG. 2, annealing may be performed in the presence of carbon dioxide (Block 400). According to other embodiments of the present invention, annealing may be preceded by immersing the polymeric material in carbon dioxide (Block 500).

According to embodiments of the present invention, annealing may be performed in the presence of a nucleating agent disposed on or within the polymeric material (Block 600). As known to those skilled in the art, nucleating agents are chemical substances which when incorporated in polymer materials form nuclei for the growth of crystals in the polymer melt. For example, in certain polymers, a higher degree of crystallinity and more uniform crystalline structure may be obtained by adding a nucleating agent.

According to other embodiments of the present invention, molecular crosslinking of the polymeric material may be modified by subjecting the polymeric material to chemical treatment and/or irradiation (Block 700). The polymeric material may be subjected to chemical treatment and/or irradiation before, during and/or after annealing. Crosslinking can impact the degree and nature of elution of pharmacological agents from an intraluminal prosthesis by increasing the tortuosity of the diffusional pathway and by slowing down the erosion rate of the prosthesis. Moreover, crosslinking can impact the deployment and/or deformation characteristics during deployment of an intraluminal prosthesis. Crosslinking can also impact the degree and nature of biodegration/bioabsorption characteristics of a polymeric intraluminal prosthesis.

Subjecting the polymeric material to chemical treatment (Block 700) may include subjecting the polymeric material to multifunctional cross-linking agents such as formaldehyde, difunctional dialdehyde, and diisocyantes. Subjecting the polymeric material to chemical treatment may include subjecting the polymeric material to enzymatic cross-linking agents such as polyethylene glycols (PEG) functionalized with a glutaminamide and a lysine-containing polypeptide using a natural tissue enzyme, and transglutaminase.

Subjecting the polymeric material to irradiation (Block 700) may include subjecting the polymeric material to ionizing radiation such as e-beam irradiation or gamma irradiation. These procedures may be done in concert as a sterilization step. UV/visible irradiation may be utilized with additives such as sensitizers and/or photoacid generators. Typical photoacid generators include dinitrobenzyltosylates, sulfonium salts, iodonium salts, diazodisulfone derivatives and sulfonates, etc. and are available from sources such as Wako Chemicals USA, Inc., 1600 Bellwood Road, Richmond, Va. 23237 USA.

Figure 4:
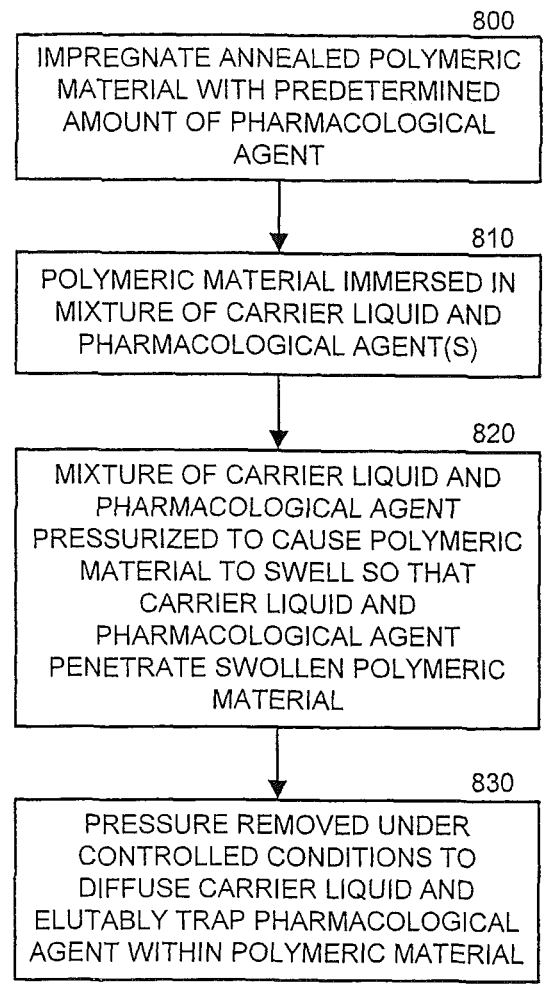

Referring to FIG. 4, methods of impregnating annealed polymeric intraluminal prostheses with one or more pharmacological agents (Block 800) are illustrated. According to embodiments of the present invention, an intraluminal prosthesis is immersed in a mixture of carrier fluid and pharmacological agent(s) (Block 810). One or more pharmacological agents may be infused within the annealed polymeric material of an intraluminal prosthesis or within an annealed polymeric coating surrounding an intraluminal prosthesis.

The carrier fluid may be a gas, liquid, or supercritical fluid. The carrier fluid may be heterogeneous or homogeneous in composition, i.e., may be a single phase composition or contain one or more additional phases, such as in the form of a microemulsion, emulsion, dispersion, suspension, etc. The carrier fluid may comprise, consist of, or consist essentially of carbon dioxide. Where multiple phases are found in the carrier fluid, carbon dioxide may be the continuous phase. One or more other ingredients may be included in the carrier fluid, such as co-solvents (i.e., water or organic co-solvents such as ethanol and methanol), surfactants or the like may be included. Where one or more organic co-solvents are included, it or they may be polar or nonpolar (or at least one of each). Where one or more surfactants are included it or they may comprise a carbon dioxide-philic group coupled to either a lipophilic (hydrophobic) or hydrophilic group, a conventional surfactant comprising a liphophilic (hydrophobic) group coupled to a hydrophilic group, or one or more of each. The carrier fluid may comprise at least 30, 40, 50, 60, 70, 80 or 90 percent by weight of carbon dioxide. When water is present in the carrier fluid, the water may comprise from about 0.01, 0.1, or 0.5 to about 1, 5, 10 or 20 percent by weight of the composition, or more.

If a plurality of pharmacological agents are utilized, the plurality of pharmacological agents may be homogeneously distributed on and/or within the intraluminal prosthesis polymeric material, or heterogeneously distributed on and/or within the intraluminal prosthesis polymeric material.

Pharmacological agents, according to embodiments of the present invention, may be hydrophilic or hydrophobic. For hydrophilic pharmacological agents, the carrier fluid may be water. For hydrophobic pharmacological agents, the carrier fluid may be a supercritical fluid, such as carbon dioxide, or it may be a liquefied gas such as carbon dioxide, CFC, HCFL, etc. An exemplary hydrophobic pharmacological agent according to embodiments of the present invention is everolimus. Everolimus is a proliferation inhibitor that targets primary causes of chronic rejection in organ transplantation patients and may also be effective for the prevention of restenosis.

According to embodiments of the present invention, carbon dioxide may be employed as a fluid in a liquid, gaseous, or supercritical phase. If liquid carbon dioxide is used, the temperature employed during the process is typically below 31° C. If gaseous carbon dioxide is used, the phase may be employed at high pressure. As used herein, the term "high pressure" generally refers to carbon dioxide having a pressure from about 50 to about 500 bar. Carbon dioxide may be utilized in a "supercritical" phase. As used herein, the term "supercritical" means that a fluid medium is above its critical temperature and pressure, i.e., about 31° C. and about 71 bar for carbon dioxide. The thermodynamic properties of carbon dioxide are reported in Hyatt, J. Org. Chem. 49: 5097-5101 (1984), and are well known to those skilled in the art.

Typically, supercritical fluids are gases at ambient temperature and pressure. However, when maintained at or above its critical point, a supercritical fluid displays properties of both a gas and a liquid. In particular, a supercritical fluid has the solvent characteristics of a liquid, but the low surface tension of a gas. Accordingly, as with a gas, a supercritical fluid can more readily diffuse into polymeric material. While any of a variety of supercritical fluids may be utilized in accordance with embodiments of the present invention, carbon dioxide is a particularly desirable supercritical fluid because it is substantially non-reactive and nontoxic (i.e., inert).

Carbon dioxide is non-toxic, non-flammable, chemically inert, completely recoverable, abundant and inexpensive. Carbon dioxide has properties that are between those of many liquids and gases. At room temperature and above its vapor pressure, carbon dioxide exists as a liquid with a density comparable to organic solvents but with excellent wetting properties and a very low viscosity. Above its critical temperature and pressure (31° C. and 71 bar), carbon dioxide is in the supercritical state and has gas-like viscosities and liquid-like densities. Small changes in temperature or pressure cause dramatic changes in the density, viscosity, and dielectric properties of supercritical carbon dioxide, making it an unusually tunable, versatile, and selective solvent.

Still referring to FIG. 4, the mixture of carrier fluid and pharmacological agent is pressurized for a time sufficient to cause the polymeric material of the intraluminal prosthesis to swell such that the carrier fluid and pharmacological agent at least partially penetrate the swollen polymeric material (Block 820). According to embodiments of the present invention, pressure can be added by the use of pressurized carbon dioxide, or by the use of a different second pressurized gas. A different second pressurized gas, such as one or more inert gases, may be helium, nitrogen, argon, etc., or combinations thereof.

For pharmacological agents soluble in carbon dioxide (e.g., hydrophobic agents), carbon dioxide may be utilized as both the carrier fluid and the pressurizing medium. For pharmacological agents not soluble in carbon dioxide (e.g., hydrophilic agents), the pharmacological agent and carrier fluid may be pressurized by an overlying blanket of carbon dioxide. Carbon dioxide is well known to those skilled in the art to be capable of swelling and plasticizing polymeric materials. Carbon dioxide is capable of partitioning into polymeric materials that are in its presence. When this occurs it can dramatically lower the glass transition temperature of the amorphous phase of the polymer. When this occurs, the diffusivity of a third component can increase dramatically. Such plasticization can enable the partitioning of third components, like a pharmaceutical agent, into the polymeric material. Conventionally, heat is required to increase glass transition temperature. Unfortunately, heating can be damaging to pharmaceutical agents that are thermally labile.

Pressure is then removed such that the carrier fluid diffuses out of the swollen polymeric material and such that a predetermined amount of the pharmacological agent remains elutably trapped within the polymeric material (Block 830). The term "elutably trapped" means that the pharmacological agent is disposed within the polymeric material in such a way that it can elute (at a predetermined rate) therefrom when the intraluminal prosthesis is deployed within the body of a subject.

The step of removing pressure (Block 830) is carried out under controlled conditions after a predetermined time and according to a predetermined schedule to insure that the desired predetermined amount of the pharmacological agent(s) remains. Controlled conditions include controlling one or more of the following parameters in a predetermined pattern: temperature, rate of temperature change, pressure, rate of pressure change, carrier fluid quantity, concentration of the pharmacological agent in the carrier fluid, etc. Loading a polymeric intraluminal prosthesis, such as a stent, or a polymeric coating on an intraluminal prosthesis can be from 0.0001 wt % to 30 wt %. However, loading at higher weight-percentages are possible (i.e., >30 wt %). These parameters can control the concentration of the pharmacological agent(s) entrapped within the polymeric material after depressurization has been achieved. Moreover, as these parameters are varied, concentration gradients of the pharmacological agent(s) entrapped within the polymeric material after depressurization can be achieved. Such concentration gradients can give rise to modified elution profiles of the pharmacological agent(s).

Embodiments of the present invention described above may be carried out using apparatus known to those skilled in the art. An exemplary apparatus for use in impregnating intraluminal prostheses with pharmacological agents is illustrated and described in U.S. Pat. No. 5,808,060 to Perman et al., which is incorporated herein by reference in its entirety.

Selective annealing may be performed so as to selectively increase (or vary) crystallinity of one or more isolated portions of the polymeric material of an intraluminal prosthesis. This will allow for customization of intraluminal prostheses and allow for matching to anatomical and physiological environments. For example, crystallinity can be increased in a mid section of an intraluminal prosthesis to enhance mechanical strength and scaffolding capability thereof, while leaving the ends of the intraluminal prosthesis more compliant so as to match the physical compliance of the non-diseased vessel wall.

According to embodiments of the present invention, selective annealing may be performed by applying a mask to one or more portions of an intraluminal prosthesis. The mask acts as a barrier to carbon dioxide absorption, thereby allowing non-masked portions to absorb carbon dioxide and to be crystallized thereby. According to other embodiments of the present invention, selective annealing may be performed by only heating selected areas of an intraluminal prosthesis. For example, a light source or a mild laser may be utilized to heat selected areas of an intraluminal prosthesis. According to other embodiments of the present invention, selective annealing may be performed by adding chemical crosslink agents only to certain areas of the polymeric material of an intraluminal prosthesis.

According to other embodiments of the present invention, selective annealing may be performed by selectively subjecting the polymeric material of an intraluminal prosthesis to irradiation, such as e-beam irradiation and gamma irradiation.

Intraluminal prostheses provided in accordance with embodiments of the present invention may be employed in sites of the body other than the vasculature including, but not limited to, biliary tree, esophagus, bowels, tracheo-bronchial tree, urinary tract, organs, etc.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A method of manufacturing an intraluminal prosthesis having an outer surface of polymeric material, wherein the intraluminal prosthesis is expandable from a contracted configuration when deployed within a lumen of a subject body, the method comprising annealing a selected portion of the polymeric material for a time prior to deployment and at a temperature sufficient to selectively modify the crystallinity thereof, wherein annealing comprises heating the selected portion of the polymeric material via a light source to a first temperature greater than or equal to the glass transition temperature of the polymeric material for a first period of time and then quenching the selected portion of the polymeric material to a second temperature lower than the glass transition temperature for a second period of time sufficient to selectively control the crystallinity of the selected portion of the polymeric material.

2. The method of claim 1, wherein the light source is a laser.

3. The method of claim 1, wherein the selected portion of the polymeric material comprises a plurality of selected portions of the polymeric material.

4. The method of claim 1, wherein annealing selectively increases the crystallinity of the selected portion of the polymeric material.

5. The method of claim 1, wherein the first temperature is higher than the melting temperature of the polymeric material.

6. The method of claim 1, wherein annealing selectively increases or decreases the modulus of the selected portion of the polymeric material.

7. The method of claim 1, wherein annealing selectively increases or decreases the hoop strength of the intraluminal prosthesis.

8. The method of claim 1, wherein annealing selectively modifies an elution rate of a pharmacological agent subsequently elutably trapped within the selected portion of the polymeric material.

9. The method of claim 1, wherein annealing selectively affects heat sensitive agents within the selected portion of the polymeric material.

10. The method of claim 8, wherein the elution rate is increased.

11. The method of claim 8, wherein the elution rate is decreased.

12. The method of claim 1, wherein annealing selectively decreases stress in the intraluminal prosthesis.

13. The method of claim 1, wherein annealing selectively increases stress in the intraluminal prosthesis.

14. The method of claim 1, wherein the polymeric material is configured to erode at a first rate when deployed within a lumen of a subject body, and wherein annealing selectively modifies the selected portion of the polymeric material such that it erodes at a second rate that is greater than the first rate when deployed within a lumen of a subject body.

15. The method of claim 1, wherein the polymeric material is configured to erode at a first rate when deployed within a lumen of a subject body, and wherein annealing selectively modifies the selected portion of the polymeric material such that it erodes at a third rate that is less than the first rate when deployed within a lumen of a subject body.

16. The method of claim 1, wherein annealing is performed in the presence of carbon dioxide.

17. The method of claim 1, wherein annealing is preceded by immersing the polymeric material in carbon dioxide.

18. The method of claim 1, wherein annealing is performed in the presence of a nucleating agent disposed on or within the polymeric material.

19. The method of claim 1, further comprising modifying molecular crosslinking of the polymeric material by subjecting the polymeric material to chemical treatment.

20. The method of claim 19, wherein subjecting the polymeric material to chemical treatment comprises subjecting the polymeric material to one or more multifunctional cross-linking agents.

21. The method of claim 20, wherein the one or more multifunctional cross-linking agents are selected from the group consisting of formaldehyde, difunctional dialdehyde, and diisocyantes.

22. The method of claim 21, wherein subjecting the polymeric material to chemical treatment comprises subjecting the polymeric material to one or more enzymatic cross-linking agents.

23. The method of claim 22, wherein the one or more enzymatic crosslinking agents are selected from the group consisting of polyethylene glycols (PEG) functionalized with a glutaminamide and a lysine-containing polypeptide using a natural tissue enzyme, and transglutaminase.

24. The method of claim 19, wherein the polymeric material is subjected to chemical treatment during annealing.

25. The method of claim 19, wherein the polymeric material is subjected to chemical treatment after annealing.

26. The method of claim 1, further comprising modifying molecular crosslinking of the polymeric material by subjecting the polymeric material to irradiation.

27. The method of claim 1, further comprising sterilizing the polymeric material by subjecting the polymeric material to irradiation.

28. The method of claim 26, wherein radiation utilized to modify molecular crosslinking is selected from the group consisting of ionizing radiation and UV/visible radiation.

29. The method of claim 27, wherein ionizing irradiation comprises e-beam irradiation or gamma irradiation.

30. The method of claim 26, wherein radiation utilized to modify molecular crosslinking comprises UV/visible radiation in the presence of a photoacid generator.

31. The method of claim 30, wherein the photoacid generator is selected from the group consisting of dinitrobenzyltosylates, sulfonium salts, iodonium salts, diazodisulfone derivatives and sulfonates.

32. The method of claim 26, wherein the polymeric material is subjected to irradiation during annealing.

33. The method of claim 26, wherein the polymeric material is subjected to irradiation after annealing.

34. The method of claim 1, wherein the intraluminal prosthesis is a stent.

35. The method of claim 1, wherein the polymeric material is erodible.

36. The method of claim 1, wherein the polymeric material is non-erodible.

37. The method of claim 1, wherein the polymeric material is a coating on the intraluminal prosthesis.

38. The method of claim 35, wherein the erodible polymeric material is selected from the group consisting of, surgical gut, silk, cotton, poly(hydroxybutyrate), polycarbonate, polyacrylate, polyanhydride, poly(ortho esters), poly(phosphoesters), polyesters, polyamides, polyphosphazenes, poly(p-dioxane), poly(amino acid), polyglactin, erodable hydrogels, collagen, chitosan, poly(lactic acid), poly(L-lactic acid), poly(D,L-lactic acid), poly(glycolic acid), poly(D-lactic-co-glycolic acid), poly(L-lactic-co-glycolic acid), poly (D,L-lactic-co-glycolic acid), poly($\epsilon$-caprolactone), poly(valerolactone), poly(hydroxy butyrate), poly(hydrovalerate), polydioxanone, polypropylene fumarate), poly(ethyleneoxide)-poly(butylenetetraphthalate), poly(lactic acid-co-lysine), poly(lactic acid-co-trimethylene carbonate), poly(L-lactic acid) and poly($\epsilon$-caprolactone) copolymers.

39. The method of claim 35, wherein the erodible polymeric material comprises a blend of polymeric material selected from the group consisting of, surgical gut, silk, cotton, poly(hydroxybutyrate), polycarbonate, polyacrylate, polyanhydride, poly(ortho esters), poly(,phosphoesters), polyesters, polyamides, polyphosphazenes, poly(p-dioxane), poly(amino acid), polyglactin, erodable hydrogels, collagen, chitosan, poly(lactic acid), poly(L-lactic acid), poly(D,L-lactic acid), poly(glycolic acid), poly(D-lactic-co-glycolic acid), poly(L-lactic-co-glycolic acid), poly (D,L-lactic-co-glycolic acid), poly($\epsilon$-caprolactone), poly(valerolactone), poly(hydroxy butyrate), poly(hydrovalerate), polydioxanone, polypropylene fumarate), poly(ethyleneoxide)-poly(butylenetetraphthalate), poly(lactic acid-co-lysine), poly(lactic acid-co-trimethylene carbonate), poly(L-lactic acid) and poly($\epsilon$-caprolactone) copolymers.

40. The method of claim 1, further comprising the step of impregnating the polymeric material with a predetermined amount of a pharmacological agent after annealing.

41. The method of claim 40, wherein impregnating the polymeric material with a predetermined amount of a pharmacological agent comprises: immersing the intraluminal prosthesis in a mixture of a carrier fluid and a pharmacological agent; pressurizing the mixture for a time sufficient to cause the polymeric material to swell such that the carrier fluid and pharmacological agent at least partially penetrate the swollen polymeric material; and removing the pressure such that the carrier fluid diffuses out of the swollen polymeric material and such that a predetermined amount of the pharmacological agent remains elutably trapped within the polymeric material.

42. The method of claim 41, wherein the carrier fluid is carbon dioxide, and wherein the pharmacological agent is hydrophobic.

43. The method of claim 42, wherein the pharmacological agent is selected from the group consisting of antineoplastics, antimitotics, antiinflammatories, antiplatelets, anticoagulants, antifibrins, antithrombins, antiproliferatives, antibiotics, antioxidants, immunosuppressives, antiallergic substances, and combinations thereof.

44. The method of claim 41, wherein the carrier fluid is water, and wherein the pharmacological agent is hydrophilic.

45. The method of claim 44, wherein pressurizing the mixture of carrier fluid and pharmacological agent comprises subjecting the mixture of carrier fluid and pharmacological agent to pressurized carbon dioxide.

46. The method of claim 42, wherein the carbon dioxide is present in a supercritical state.

47. The method of claim 46, wherein the carbon dioxide contains a co-solvent.

48. The method of claim 47, wherein the co-solvent is selected from the group consisting of ethanol and methanol.

49. A method of manufacturing an intraluminal prosthesis having an outer surface of polymeric material, wherein the intraluminal prosthesis is expandable from a contracted configuration when deployed within a lumen of a subject body, the method comprising:
   annealing a selected portion of the polymeric material via a light source for a time prior to deployment and at a temperature sufficient to selectively modify the crystallinity thereof; and
   modifying molecular crosslinking of the selected portion of the polymeric material by subjecting the polymeric material to irradiation, wherein the selected portion of the polymeric material is subjected to irradiation during annealing.

50. The method of claim 49, wherein the light source is a laser.

51. The method of claim 49, wherein the selected portion of the polymeric material comprises a plurality of selected portions of the polymeric material.

52. The method of claim 49, wherein annealing comprises heating the selected portion of the polymeric material to a temperature between the glass transition temperature and the melting temperature of the polymeric material for a period of time sufficient to selectively increase or decrease one or more of the following: the crystallinity of the selected portion of the polymeric material, the modulus of the selected portion of the polymeric material, the hoop strength of the intraluminal prosthesis, the elution rate of a pharmacological agent subsequently elutably trapped within the selected portion of the polymeric material, stress in the intraluminal prosthesis.

53. The method of claim 49, wherein annealing comprises heating the selected portion of the polymeric material to a temperature between the glass transition temperature and the melting temperature of the polymeric material for a period of time sufficient to selectively affect heat sensitive agents within the polymeric material.

54. The method of claim 49, wherein the polymeric material is configured to erode at a first rate when deployed within a lumen of a subject body, and wherein annealing comprises heating the selected portion of the polymeric material to a temperature between the glass transition temperature and the melting temperature of the polymeric material for a period of time sufficient to selectively modify the selected portion of the polymeric material such that it erodes at a second rate that is greater than the first rate when deployed within a lumen of a subject body.

55. The method of claim 49, wherein the polymeric material is configured to erode at a first rate when deployed within a lumen of a subject body, and wherein annealing comprises heating the selected portion of the polymeric material to a temperature between the glass transition temperature and the melting temperature of the polymeric material for a period of time sufficient to selectively modify the selected portion of the polymeric material such that it erodes at a third rate that is less than the first rate when deployed within a lumen of a subject body.

56. The method of claim 49, wherein annealing is performed in the presence of carbon dioxide.

57. The method of claim 49, wherein annealing is preceded by immersing the polymeric material in carbon dioxide.

58. The method of claim 49, wherein annealing is performed in the presence of a nucleating agent disposed on or within the polymeric material.

59. The method of claim 49, further comprising sterilizing the polymeric material by subjecting the polymeric material to irradiation.

60. The method of claim 49, wherein radiation utilized to modify molecular crosslinking is selected from the group consisting of ionizing radiation and UV/visible radiation.

61. The method of claim 60, wherein ionizing irradiation comprises e-beam irradiation or gamma irradiation.

62. The method of claim 49, wherein radiation utilized to modify molecular crosslinking comprises UV/visible radiation in the presence of a photoacid generator.

63. The method of claim 62, wherein the photoacid generator is selected from the group consisting of dinitrobenzyltosylates, sulfonium salts, iodonium salts, diazodisulfone derivatives and sulfonates.

64. The method of claim 49, wherein the intraluminal prosthesis is a stent.

65. The method of claim 49, wherein the polymeric material is erodible.

66. The method of claim 49, wherein the polymeric material is non-erodible.

67. The method of claim 49, wherein the polymeric material is a coating on the intraluminal prosthesis.

68. The method of claim 65, wherein the erodible polymeric material is selected from the group consisting of surgical gut, silk, cotton, poly(hydroxybutyrate), polycarbonate, polyacrylate, polyanhydride, poly(ortho esters), poly(phosphoesters), polyesters, polyamides, polyphosphazenes, poly(p-dioxane), poly(amino acid), polyglactin, erodable hydrogels, collagen, chitosan, poly(lactic acid), poly(L-lactic acid), poly(D,L-lactic acid), poly(glycolic acid), poly(D-lactic-co-glycolic acid), poly(L-lactic-co-glycolic acid), poly (D,L-lactic-co-glycolic acid), poly($\epsilon$-caprolactone), poly(valerolactone), poly(hydroxy butyrate), poly(hydrovalerate), polydioxanone, poly(propylene fumarate), poly(ethyleneoxide)-poly(butylenetetraphthalate), poly(lactic acid-co-lysine), poly(lactic acid-co-trimethylene carbonate), poly(L-lactic acid) and poly(s-caprolactone) copolymers.

69. The method of claim 65, wherein the erodible polymeric material comprises a blend of polymeric material selected from the group consisting of, surgical gut, silk, cotton, poly(hydroxybutyrate), polycarbonate, polyacrylate, polyanhydride, poly(ortho esters), poly(phosphoesters), polyesters, polyamides, polyphosphazenes, poly(p-dioxane), poly(amino acid), polyglactin, erodable hydrogels, collagen, chitosan, poly(lactic acid), poly(L-lactic acid), poly(D,L-lactic acid), poly(glycolic acid), poly(D-lactic-co-glycolic acid), poly(L-lactic-co-glycolic acid), poly (D,L-lactic-co-glycolic acid), poly($\epsilon$-caprolactone), poly(valerolactone), poly(hydroxy butyrate), poly(hydrovalerate), polydioxanone, poly(propylene fumarate), poly(ethyleneoxide)-poly(butylenetetraphthalate), poly(lactic acid-co-lysine), poly(lactic acid-co-trimethylene carbonate), poly(L-lactic acid) and poly($\epsilon$-caprolactone) copolymers.

70. The method of claim 49, further comprising the step of impregnating the polymeric material with a predetermined amount of a pharmacological agent after annealing.

71. The method of claim 70, wherein impregnating the polymeric material with a predetermined amount of a pharmacological agent comprises: immersing the intraluminal prosthesis in a mixture of a carrier fluid and a pharmacological agent; pressurizing the mixture for a time sufficient to cause the polymeric material to swell such that the carrier fluid and pharmacological agent at least partially penetrate the swollen polymeric material; and removing the pressure such that the carrier fluid diffuses out of the swollen polymeric material and such that a predetermined amount of the pharmacological agent remains elutably trapped within the polymeric material.

72. The method of claim 71, wherein the carrier fluid is carbon dioxide, and wherein the pharmacological agent is hydrophobic.

73. The method of claim 72, wherein the pharmacological agent is selected from the group consisting of antineoplastics, antimitotics, antiinflammatories, antiplatelets, anticoagulants, antifibrins, antithrombins, antiproliferatives, antibiotics, antioxidants, immunosuppressives, antiallergic substances, and combinations thereof.

74. The method of claim 70, wherein the carrier fluid is water, and wherein the pharmacological agent is hydrophilic.

75. The method of claim 74, wherein pressurizing the mixture of carrier fluid and pharmacological agent comprises subjecting the mixture of carrier fluid and pharmacological agent to pressurized carbon dioxide.

76. The method of claim 72, wherein the carbon dioxide is present in a supercritical state.

77. The method of claim 76, wherein the carbon dioxide contains a co-solvent.

78. The method of claim 77, wherein the co-solvent is selected from the group consisting of ethanol and methanol.

79. A method of manufacturing an intraluminal prosthesis having an outer surface of polymeric material, wherein the intraluminal prosthesis is expandable from a contracted configuration when deployed within a lumen of a subject body, the method comprising:
    annealing a selected portion of the polymeric material via a light source for a time prior to deployment and at a temperature sufficient to selectively modify the crystallinity thereof; and
    modifying molecular crosslinking of the polymeric material by subjecting the selected portion of the polymeric material to irradiation, wherein the selected portion of the polymeric material is subjected to irradiation after annealing.

80. The method of claim 79, wherein the light source is a laser.

81. The method of claim 79, wherein the selected portion of the polymeric material comprises a plurality of selected portions of the polymeric material.

82. The method of claim 79, wherein annealing comprises heating the selected portion of the polymeric material to a temperature between the glass transition temperature and the melting temperature of the polymeric material for a period of time sufficient to selectively increase or decrease one or more of the following: the crystallinity of the selected portion of the polymeric material, the modulus of the selected portion of the polymeric material, the hoop strength of the intraluminal prosthesis, the elution rate of a pharmacological agent subsequently elutably trapped within the selected portion of the polymeric material, stress in the intraluminal prosthesis.

83. The method of claim 79, wherein annealing comprises heating the selected portion of the polymeric material to a temperature between the glass transition temperature and the melting temperature of the polymeric material for a period of time sufficient to selectively affect heat sensitive agents within the polymeric material.

84. The method of claim 79, wherein the polymeric material is configured to erode at a first rate when deployed within a lumen of a subject body, and wherein annealing comprises heating the selected portion of the polymeric material to a temperature between the glass transition temperature and the melting temperature of the polymeric material for a period of time sufficient to selectively modify the selected portion of the polymeric material such that it erodes at a second rate that is greater than the first rate when deployed within a lumen of a subject body.

85. The method of claim 79, wherein the polymeric material is configured to erode at a first rate when deployed within a lumen of a subject body, and wherein annealing comprises heating the selected portion of the polymeric material to a temperature between the glass transition temperature and the melting temperature of the polymeric material for a period of time sufficient to selectively modify the selected portion of the polymeric material such that it erodes at a third rate that is less than the first rate when deployed within a lumen of a subject body.

86. The method of claim 79, wherein annealing is performed in the presence of carbon dioxide.

87. The method of claim 79, wherein annealing is preceded by immersing the polymeric material in carbon dioxide.

88. The method of claim 79, wherein annealing is performed in the presence of a nucleating agent disposed on or within the polymeric material.

89. The method of claim 79, further comprising sterilizing the polymeric material by subjecting the polymeric material to irradiation.

90. The method of claim 79, wherein radiation utilized to modify molecular crosslinking is selected from the group consisting of ionizing radiation and UV/visible radiation.

91. The method of claim 90, wherein ionizing irradiation comprises e-beam irradiation or gamma irradiation.

92. The method of claim 79, wherein radiation utilized to modify molecular crosslinking comprises UV/visible radiation in the presence of a photoacid generator.

93. The method of claim 92, wherein the photoacid generator is selected from the group consisting of dinitrobenzyltosylates, sulfonium salts, iodonium salts, diazodisulfone derivatives and sulfonates.

94. The method of claim 79, wherein the intraluminal prosthesis is a stent.

95. The method of claim 79, wherein the polymeric material is erodible.

96. The method of claim 79, wherein the polymeric material is non-erodible.

97. The method of claim 79, wherein the polymeric material is a coating on the intraluminal prosthesis.

98. The method of claim 95, wherein the erodible polymeric material is selected from the group consisting of, surgical gut, silk, cotton, poly(hydroxybutyrate), polycarbonate, polyacrylate, polyanhydride, poly(ortho esters), poly(phosphoesters), polyesters, polyamides, polyphosphazenes, poly (p-dioxane), poly(amino acid), polyglactin, erodable hydrogels, collagen, chitosan, poly(lactic acid), poly(L-lactic acid), poly(D,L-lactic acid), poly(glycolic acid), poly(D-lactic-co-glycolic acid), poly(L-lactic-co-glycolic acid), poly (D,L-lactic-co-glycolic acid), poly($\epsilon$-caprolactone), poly(valerolactone), poly(hydroxy butyrate), poly(hydrovalerate), polydioxanone, polypropylene fumarate), poly(ethyleneoxide)-poly(butylenetetraphthalate), poly(lactic acid-co-lysine), poly(lactic acid-co-trimethylene carbonate), poly(L-lactic acid) and poly($\epsilon$-caprolactone) copolymers.

99. The method of claim 95, wherein the erodible polymeric material comprises a blend of polymeric material selected from the group consisting of, surgical gut, silk, cotton, poly(hydroxybutyrate); polycarbonate, polyacrylate, polyanhydride, poly(ortho esters), poly(phosphoesters), polyesters, polyamides, polyphosphazenes, poly(p-dioxane), poly(amino acid), polyglactin, erodable hydrogels, collagen, chitosan, poly(lactic acid), poly(L-lactic acid), poly(D,L-lactic acid), poly(glycolic acid), poly(D-lactic-co-glycolic acid), poly(L-lactic-co-glycolic acid), poly (D,L-lactic-co-glycolic acid), poly($\epsilon$-caprolactone), poly(valerolactone), poly(hydroxy butyrate), poly(hydrovalerate), polydioxanone, polypropylene fumarate), poly(ethyleneoxide)-poly(butylenetetraphthalate), poly(lactic acid-co-lysine), poly(lactic acid-co-trimethylene carbonate), poly(L-lactic acid) and poly ($\epsilon$-caprolactone) copolymers.

100. The method of claim 79, further comprising the step of impregnating the polymeric material with a predetermined amount of a pharmacological agent after annealing.

101. The method of claim 100, wherein impregnating the polymeric material with a predetermined amount of a pharmacological agent comprises: immersing the intraluminal prosthesis in a mixture of a carrier fluid and a pharmacological agent; pressurizing the mixture for a time sufficient to cause the polymeric material to swell such that the carrier fluid and pharmacological agent at least partially penetrate the swollen polymeric material; and removing the pressure such that the carrier fluid diffuses out of the swollen polymeric material and such that a predetermined amount of the pharmacological agent remains elutably trapped within the polymeric material.

102. The method of claim 101, wherein the carrier fluid is carbon dioxide, and wherein the pharmacological agent is hydrophobic.

103. The method of claim 102, wherein the pharmacological agent is selected from the group consisting of antineoplastics, antimitotics, antiinflammatories, antiplatelets, anticoagulants, antifibrins, antithrombins, antiproliferatives, antibiotics, antioxidants, immunosuppressives, antiallergic substances, and combinations thereof.

104. The method of claim 101, wherein the carrier fluid is water, and wherein the pharmacological agent is hydrophilic.

105. The method of claim 104, wherein pressurizing the mixture of carrier fluid and pharmacological agent comprises subjecting the mixture of carrier fluid and pharmacological agent to pressurized carbon dioxide.

106. The method of claim 102, wherein the carbon dioxide is present in a supercritical state.

107. The method of claim 106, wherein the carbon dioxide contains a co-solvent.

108. The method of claim 107, wherein the co-solvent is selected from the group consisting of ethanol and methanol.

* * * * *

UNITED STATES PATENT AND TRADEMARK OFFICE
CERTIFICATE OF CORRECTION

PATENT NO. : 8,906,286 B2  
APPLICATION NO. : 13/075483  
DATED : December 9, 2014  
INVENTOR(S) : DeSimone et al.

Page 1 of 1

It is certified that error appears in the above-identified patent and that said Letters Patent is hereby corrected as shown below:

In the Specification:
Column 2, Line 60: Please correct "<$T_g$)" to read -- <$T_g$). --

In the Claims:
Column 15, Claim 38, Line 14: Please correct "polypropylene fumarate)," to read -- poly(propylene fumarate), --

Column 15, Claim 39, Line 30: Please correct "polypropylene fumarate)," to read -- poly(propylene fumarate), --

Column 19, Claim 98, Line 55: Please correct "polypropylene fumarate)," to read -- poly(propylene fumarate), --

Column 20, Claim 99, Line 15: Please correct "polypropylene fumarate)," to read -- poly(propylene fumarate), --

Signed and Sealed this  
Fifth Day of May, 2015

Michelle K. Lee  
*Director of the United States Patent and Trademark Office*